United States Patent [19]
Anderson et al.

[11] 3,943,241
[45] Mar. 9, 1976

[54] CARIOSTATIC COMPOSITION

[75] Inventors: Ray H. Anderson, Osseo; Albert L. Saari, Minneapolis, both of Minn.

[73] Assignee: General Mills, Inc., Minneapolis, Minn.

[22] Filed: Aug. 30, 1971

[21] Appl. No.: 176,275

[52] U.S. Cl. .................................. 424/54
[51] Int. Cl.² ............................. A61K 7/22
[58] Field of Search ................... 424/54, 199

[56] References Cited
UNITED STATES PATENTS
3,231,388  1/1966  White .............................. 99/92

OTHER PUBLICATIONS
Gould, *Dietary Chemicals vs. Dental Caries*, published by American Chemical Soc., Washington, 1970, p. 28.

*Chemical Abstracts* (1), Vol. 45, entry 197g, 1951.

*Chemical Abstracts* (2), Vol. 58, entry 10303h, 1963.

*Primary Examiner*—Richard L. Huff
*Attorney, Agent, or Firm*—Gene O. Enockson; Norman P. Friederichs

[57] ABSTRACT

A cariostatic composition is disclosed which contains an alkali metal amino acid phosphate or an alkaline earth metal amino acid phosphate. The amino acid phosphate serves as a cariostatic agent and may be used for topical application or as a dentifrice.

10 Claims, No Drawings

CARIOSTATIC COMPOSITION

The present invention relates to a cariostatic composition and more particularly a cariostatic composition including a non-toxic cariostatic agent.

In the past various types of cariostatic agents and compositions have been proposed. For example, materials such as stannous fluoride, calcium carbonate, and sodium hydrogen phosphate have been proposed for reducing dental caries. Cariostatic agents may be applied topically to the teeth, included in dentifrice compositions, or included in foods. The present invention relates to an alkaline amino acid phosphate which is suitable for topical application or use in a dentifrice. The present cariostatic agent is not toxic and in fact is nutritious providing amino acid fortification if added to a food product. Such a food product is disclosed in our patent application Ser. No. 176,276 entitled "A Food Composition" filed on even date herewith. The cariostatic composition of the present invention includes a solution and/or suspension of the alkaline amino acid phosphate. The solvent may be any of the solvents conventionally used in cariostatic compositions. The solvent may be any polyol, carbohydrate or carbohydrate syrup such as corn syrups; however, the solvent is preferably a non-fermentable polyol, carbohydrate or carbohydrate syrup such as glycerol, propylene glycol, glyceraldehyde and aqueous syrups of erythritol. The cariostatic composition may include various other materials typically found in cariostatic compositions, such as polishing agents (calcium phosphate, calcium carbonate, silicates and pumice), surface active agents (detergents and soaps), other cariostatic agents (stannous fluoride and alkali fluorophosphates), thickeners (gums), coloring and flavoring.

The cariostatic agent used in the present composition may be prepared by reacting an amino acid in the free base form with phosphoric acid to form an amino acid phosphate. The amino acid phosphate may be then reacted with a base or basic salt of an alkali metal or an alkaline earth metal to form an alkaline amino acid phosphate. In some instances the cariostatic agent may be prepared by reacting the free base amino acid directly with an alkali metal phosphate or an alkaline earth metal phosphate. The term "alkaline amino acid phosphate" as used herein includes alkali metal amino acid phosphates, alkaline earth metal amino acid phosphates and their diphosphates.

Any amino acid may be used in preparing the cariostatic agent of the present invention providing the amino acid will react to form the alkaline amino acid phosphate. The amino acids used to prepare the cariostatic agent typically include lysine, ornithine, arginine, tryptophan, phenyl alanine, leucine, isoleucine, threonine, methionine, valine, hydroxyproline and glycine. The preferred amino acid is L-lysine. The amino acid is preferably in the free base form when used to prepare the cariostatic agent. Certain of the free base amino acids, typically L-lysine, are unstable and therefore may be produced from the hydrochloride immediately prior to use in producing the cariostatic agent. The free base amino acid may be prepared by passing a water solution of the amino acid hydrochloride through a resin column in the OH⁻ ionic form. Other amino acids may be obtained commercially in the free base form. The free base amino acid may be reacted with a phosphoric acid such as orthophosphoric acid in a molar weight ratio of from 1:1 to 1:2 to produce the amino acid phosphate. Alternatively, the amino acid may be manufactured directly as the phosphate rather than hydrochloride.

The amino acid phosphate may be reacted, as a water solution, with the alkali metal compound or the alkaline earth metal compound. These compounds may be a base or basic salt. In other words the alkali metal compound may be an oxide or a hydroxide of sodium or potassium. The alkali metal compound may be a basic salt such as a carbonate or bicarbonate of sodium or potassium. The alkaline earth metal compound may be an oxide, hydroxide, carbonate or bicarbonate of calcium or magnesium. The alkali metal compound or alkaline earth metal compound may be added to the amino acid phosphate solution in the form of a dry product such as pellets or in the form of an aqueous solution.

The amino acid phosphate, in the case of basic amino acids, may be reacted with the alkali metal compound or alkaline earth metal compound in a ratio of one mole of amino acid phosphate to between one and two equivalent weights of the alkali metal compound or alkaline earth metal compound. In the case of the phosphates of neutral amino acids the ratio may be one mole of amino acid phosphate to one equivalent weight of alkali metal compound or alkaline earth metal compound.

The alkaline amino acid phosphate, used in preparing the present cariostatic composition, may be precipitated from the aqueous solution at room temperature with a water-miscible organic solvent such as methanol, ethanol, acetone or mixtures of such solvents. The precipitate may be washed with the water-miscible solvent and dried. The alkaline amino acid phosphate is preferably in a finely divided state such that it will pass through a No. 100 screen or smaller. The alkaline amino acid phosphate solution, used in preparing the present cariostatic composition, may be in the form of a solution. The solution may be concentrated by evaporation, such as vacuum drying, to a concentration of about 40 to 50% solids. The alkaline amino acid phosphate will typically be present in the cariostatic composition in an amount of from 1% to 25% by weight of solvent, preferably about 10%. The cariostatic composition will generally be prepared by working the alkaline amino acid phosphate into the solvent at room temperature or by warming to 60°C. The remaining ingredients are added and thoroughly dispersed. A typical dentifrice of the present invention may include, by weight, 32 parts precipitated calcium carbonate, 3.5 parts precipitated magnesium carbonate, 5.6 parts powdered soap, 30 parts glycerin, 26.6 parts water, 0.06 part saccharin, 0.30 part gum karaya, 0.3 part Irish Moss and 12.0 part alkaline amino acid phosphate. Flavoring and coloring may be added as desired.

The following examples are for purposes of illustrating the present invention and are not intended to be limiting.

EXAMPLE I

A cariostatic agent was prepared for use in the present invention by passing a 10% (by weight) solution of L-lysine hydrochloride through a resin column to produce free base lysine. The resin column was 20 inches in height and was an IR-410 (Amberlite) in the OH⁻ ionic form. The solution was passed through the column at the rate of 2 to 3 milliliters per square centimeter of column per minute. The free base lysine was eluted with water. One molar part of the free base lysine was added to a flask containing one molar part of orthophosphoric acid. One molar part of orthophosphoric acid was added to the aqueous solution of lysine phosphate thereby producing lysine diphosphate. One molar part of sodium hydroxide pellets was added to the lysine diphosphate. Then one molar part of potassium hydroxide pellets was added to the solution with thorough mixing. The resulting solution was evaporated to approximately 45% solids in a vacuum using a rotary evaporator. The concentrated solution of sodium potassium lysine diphosphate was found to be stable at room temperature.

EXAMPLE II

A cariostatic agent (potassium lysine phosphate), suitable for use in the present invention, was prepared by passing a 10% (by weight) L-lysine hydrochloride solution in an amount of 455 grams through the resin column as described in Example I. The resulting free base lysine was added to 3470 ml. of an aqueous solution containing 345 g. of $KH_2PO_4$. One half of the resulting solution was evaporated to about 700 ml. and then 750 ml. of methanol were added. The mixture was cooled to 5°C. and the potassium lysine phosphate precipitated. The precipitate was collected by filtration and air dried.

EXAMPLE III

A cariostatic agent (potassium lysine diphosphate) was prepared from the remaining solution of Example II by adding to such solution 85 milliliters of an 85% $H_3PO_4$ solution. The resulting solution was evaporated to 750 milliliters and 750 milliliters of methanol were added. The mixture was cooled to 5°C. and the potassium lysine diphosphate precipitated. The precipitate was collected by filtration.

EXAMPLE IV

A cariostatic agent (sodium lysine diphosphate) was prepared by passing 300 millimoles of L-lysine hydrochloride through a resin column to produce free base lysine. The resin used was Rexyn AGI in the OH⁻ form. To the free base L-lysine was added 300 millimoles of sodium dihydrogen phosphate. Then 300 millimoles of orthophosphoric acid were added with thorough stirring. The resulting solution was evaporated in a vacuum until a milky appearance was acquired and then cooled to 5°C. The material was filtered and a tacky crystalline material was obtained and air dried. The material was identified as Na Lysine $H_5(PO_4)_2$.

EXAMPLE V

A cariostatic agent K $LysH_5(PO_4)_2 \cdot LysH_6(PO_4)_2$ was prepared by adding 2.5 moles of free base lysine to 2.5 moles of $H_3PO_4$. Then 2.5 moles of $H_3PO_4$ were added. The resulting solution was divided into two equal portions A and B. To Portion A was added 0.625 equivalent weights of $K_2CO_3$. The resulting solution was found to contain K $LysH_5(PO_4)_2 \cdot LysH_6(PO_4)_2$.

EXAMPLE VI

A cariostatic agent, $K_2LysH_4(PO_4)_2$, was prepared from Portion B by the addition of 2.5 equivalent weights of $K_2CO_3$ with thorough mixing.

EXAMPLE VII

A cariostatic composition was prepared according to the present invention. One gram of $NaLysH_5(PO_4)_2$ was dissolved in 10 milliliters of glycerol. The $NaLysH_5(PO_4)_2$ was of a particle size which passed through a No. 100 screen. The resulting solution was applied to the teeth of a group of ten 12 day old Cotton rats. The topical applications were made at four 2 hour intervals. Each application was 2 drops per rat. A second group of 10 rats were used as a control group and received topical applications of glycerol rather than the $NaLysH_5(PO_4)_2$ solution. The rats were all fed an adequate diet of 12 parts starch, 18 parts sucrose, 38 parts oat groats, 32 parts whole milk powder and 2 parts liver powder, by weight. The rats were sacrificed at 30 days of age. The group treated with the $NaLysH_5(PO_4)_2$ had a 32% reduction in caries as compared to the control group. The caries concerned were sulcal caries or in other words pit and fissure carries as measured on the first and second molars.

The embodiments of the invention in which an exclusive property or privilege is claimed are defined as follows:

1. A cariostatic composition for application to teeth to reduce carries, said composition comprising a solvent and a cariostatic agent selected from the group consisting of alkali metal amino acid phosphates, alkaline earth metal amino acid phosphates and their diphosphates, said cariostatic agent being present in an amount of from 1 to 25% by weight based on the weight of the solvent.

2. The cariostatic composition of claim 1 wherein the solvent is a polyol, carbohydrate or carbohydrate syrup.

3. The cariostatic composition of claim 2 wherein the solvent is non-fermentable.

4. The cariostatic composition of claim 1 wherein the solvent is a member selected from the group consisting of glycerol and propylene glycol.

5. The cariostatic composition of claim 1 wherein the solvent is a member selected from the group consisting of glyceraldehyde and aqueous syrups of erythritol.

6. The composition of claim 1 wherein said composition further includes a polishing agent.

7. The composition of claim 6 wherein said composition further includes a surface active agent.

8. The composition of claim 1 wherein the cariostatic agent is present in an amount of about 10%.

9. The cariostatic composition of claim 1 wherein said amino acid is a member selected from the group consisting of lysine, ornithine, arginine, tryptophan, phenyl alanine, leucine, isoleucine, threnine, methionine, valine, hydroxyproline and glycine.

10. A method for reducing caries comprising applying to teeth a cariostatic composition comprising a solvent and a member selected from the group consisting of alkali metal amino acid phosphates, alkaline earth metal amino acid phosphates and their diphosphates, said member being present in an amount of from 1 to 25% by weight based on the weight of the solvent.

* * * * *

UNITED STATES PATENT OFFICE
CERTIFICATE OF CORRECTION

PATENT NO. : 3,943,241
DATED : March 9, 1976
INVENTOR(S) : Ray H. Anderson & Albert L. Saari It is certified that error appears in the above-identified patent and that said Letters Patent are hereby corrected as shown below:

Col. 4, line 56; "threnine" should be --- threonine ---.

Signed and Sealed this first Day of June 1976

[SEAL]

Attest:

RUTH C. MASON
Attesting Officer

C. MARSHALL DANN
Commissioner of Patents and Trademarks